(12) United States Patent
Takai et al.

(10) Patent No.: US 6,705,189 B2
(45) Date of Patent: Mar. 16, 2004

(54) FLEXIBLE COMPOSITE SHEET AND PROCESS FOR MAKING THE SAME

(75) Inventors: Hisashi Takai, Kagawa-ken (JP); Miou Suzuki, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 10/298,985

(22) Filed: Nov. 18, 2002

(65) Prior Publication Data

US 2003/0068467 A1 Apr. 10, 2003

Related U.S. Application Data

(62) Division of application No. 09/813,222, filed on Mar. 20, 2001, now Pat. No. 6,503,597.

(51) Int. Cl.[7] .............................. B26D 3/08; A61F 13/15
(52) U.S. Cl. .............................. 83/53; 83/177; 428/137
(58) Field of Search ...................... 28/104, 72.2; 83/53, 83/177, 861, 286, 287, 289, 298, 76.8, 22, 27, 76.6, 51, 49; 428/119, 137, 131, 132, 224, 139, 233, 234

(56) References Cited

U.S. PATENT DOCUMENTS

| | | | | |
|---|---|---|---|---|
| 3,214,819 A | * | 11/1965 | Guerin ...................... 264/119 |
| 3,769,659 A | * | 11/1973 | Kalwaites .................... 28/104 |
| 3,873,225 A | * | 3/1975 | Jakobsen et al. ............. 404/41 |
| 3,950,587 A | * | 4/1976 | Colijn et al. ................ 442/271 |
| 4,146,663 A | * | 3/1979 | Ikeda et al. ................... 428/96 |
| 4,183,987 A | * | 1/1980 | Eby et al. ................... 428/192 |
| 4,246,838 A | * | 1/1981 | Pulver et al. ................. 99/516 |
| 4,780,363 A | * | 10/1988 | Evans et al. ................ 442/388 |
| 5,397,625 A | * | 3/1995 | Osteen et al. ................. 442/35 |
| 5,840,089 A | * | 11/1998 | Chesley et al. ............... 51/295 |
| 6,117,524 A | * | 9/2000 | Hisanaka et al. ........... 428/137 |
| 2002/0061396 A1 | * | 5/2002 | White ...................... 428/293.4 |

FOREIGN PATENT DOCUMENTS

| EP | 0919212 A2 | 6/1999 | | |
|---|---|---|---|---|
| JP | 11-217453 | * | 8/1999 | .............. C08J/9/00 |

* cited by examiner

*Primary Examiner*—Allan N. Shoap
*Assistant Examiner*—Ghassem Alie
(74) *Attorney, Agent, or Firm*—Butzel Long

(57) ABSTRACT

A flexible composite sheet that includes a fibrous assembly and a plurality of narrow film strips bonded to upper surface of the fibrous assembly. The narrow strips are intermittently arranged so that the fibrous assembly may be exposed between each pair of the adjacent narrow strips. Sides defining each of the narrow strips are formed with tooth-like portions.

3 Claims, 3 Drawing Sheets

US 6,705,189 B2

FLEXIBLE COMPOSITE SHEET AND PROCESS FOR MAKING THE SAME

RELATED APPLICATION

This is a Divisional of U.S. patent application Ser. No. 09/813,222, filed on Mar. 20, 2001, now U.S. Pat. No. 6,503,597 issued Jan. 7, 2003.

BACKGROUND OF THE INVENTION

This invention relates to a flexible composite sheet suitable for use as a topsheet in a disposable body fluid absorbent sanitary article such as a disposable diaper, a sanitary napkin or the like.

Japanese Patent Application Publication No. 1999-217453A describes a flexible composite sheet comprising a flexible plastic sheet layer and a fibrous layer bonded to a lower surface of the plastic sheet layer. In this composite sheet, the plastic sheet layer is provided with a plurality of opening arrays each having a plurality of openings arranged intermittently in one direction. A plane region of plastic sheet is defined between each pair of the adjacent opening arrays and a plurality of tooth-like portions extend upward from the upper surface of the plane region along edges of the peripheries defining the respective openings, the edges extending in the one direction, so that the tooth-like portions may undulate in the one direction in the form of an irregular wave.

With the composite sheet of prior art, a plurality of the tooth-like portions are flexibly deformed and give the article wearer a velvet-like soft touch as the surface of the composite sheet comes in contact with a wearer's skin. However, most of the tooth-like portions are arranged to form the irregular waves in the same direction as the direction in which the opening arrays extend. This means that these tooth-like portions are easily collapsed orthogonally to the opening arrays and thereby give a wearer a soft touch but collapsed with a difficulty in the direction in which the opening arrays extend. Consequently, a flexibility in the latter direction is inferior to a flexibility in the former direction. Furthermore, even if such differential flexibility depending on the direction raises no serious problem for use of such composite sheet as the topsheet of the sanitary article, an anisotropy of the composite sheet with respect to its flexibility should undesirably restrict practical use of the composite sheet.

SUMMARY OF THE INVENTION

It is an object of this invention to provide a conventional composite sheet in which anisotropy in the flexibility of the sheet surface may be eliminated.

According to this invention, there is provided a composite sheet comprising a sheet-like fibrous assembly having upper and lower surfaces and a film of thermoplastic synthetic resin being intermittently arranged on and bonded to the upper surface of the sheet-like fibrous assembly so that the upper surface is exposed in a plurality of regions.

The composite sheet further comprises the fibrous assembly being formed with fibers having a fineness of 0.5~20 dtex and a basis weight of 5~60 g/m² and the film being formed by a plurality of narrow strips, each having a thickness of 1~50 µm, intermittently arranged so as to be spaced one from another by a distance of 30~1000 µmm in a first direction and in a second direction intersecting the first direction of the fibrous assembly wherein each of the narrow strips is defined by sides extending in the first and second directions, respectively, along which the narrow strip is formed with a plurality of tooth-like portions rising in a direction from the lower surface toward the upper surface and have proximal ends lying along the sides and distal ends so that the tooth-like portions are tapered from the proximal ends toward the distal ends.

Also, according to this invention, there is provided a process for making a flexible composite sheet by subjecting a composite web comprising a continuous fibrous web having upper and lower surfaces and a continuous film of thermoplastic synthetic resin bonded to the upper surface to the steps of:

a. continuously feeding the composite web in one direction;

b. reciprocating a first group of nozzles in a direction transversely of the one direction, the first group having a plurality of nozzles linearly arranged transversely of the one direction, wherein columnar fluid streams are ejected from the nozzles against the film of the composite web so that the film may be broken in accordance with loci of the nozzles being reciprocated; and c. reciprocating a second group of nozzles in a direction transversely of the one direction, the second group having a plurality of nozzles linearly arranged transversely of the one direction, wherein columnar fluid streams are ejected from the nozzles against the lower surface of the fibrous web so that broken regions of the film is widened and lengthened and portions of the film remaining along the broken regions are oriented so as to rise in a direction from the lower surface toward the upper surface of the fibrous web.

DETAILED DESCRIPTION OF THE PREFERRED EMBODIMENTS

Details of a flexible composite sheet and a process for making the same according to this invention will be more fully understood from the description given hereunder with reference to the accompanying drawings.

Figure 1:
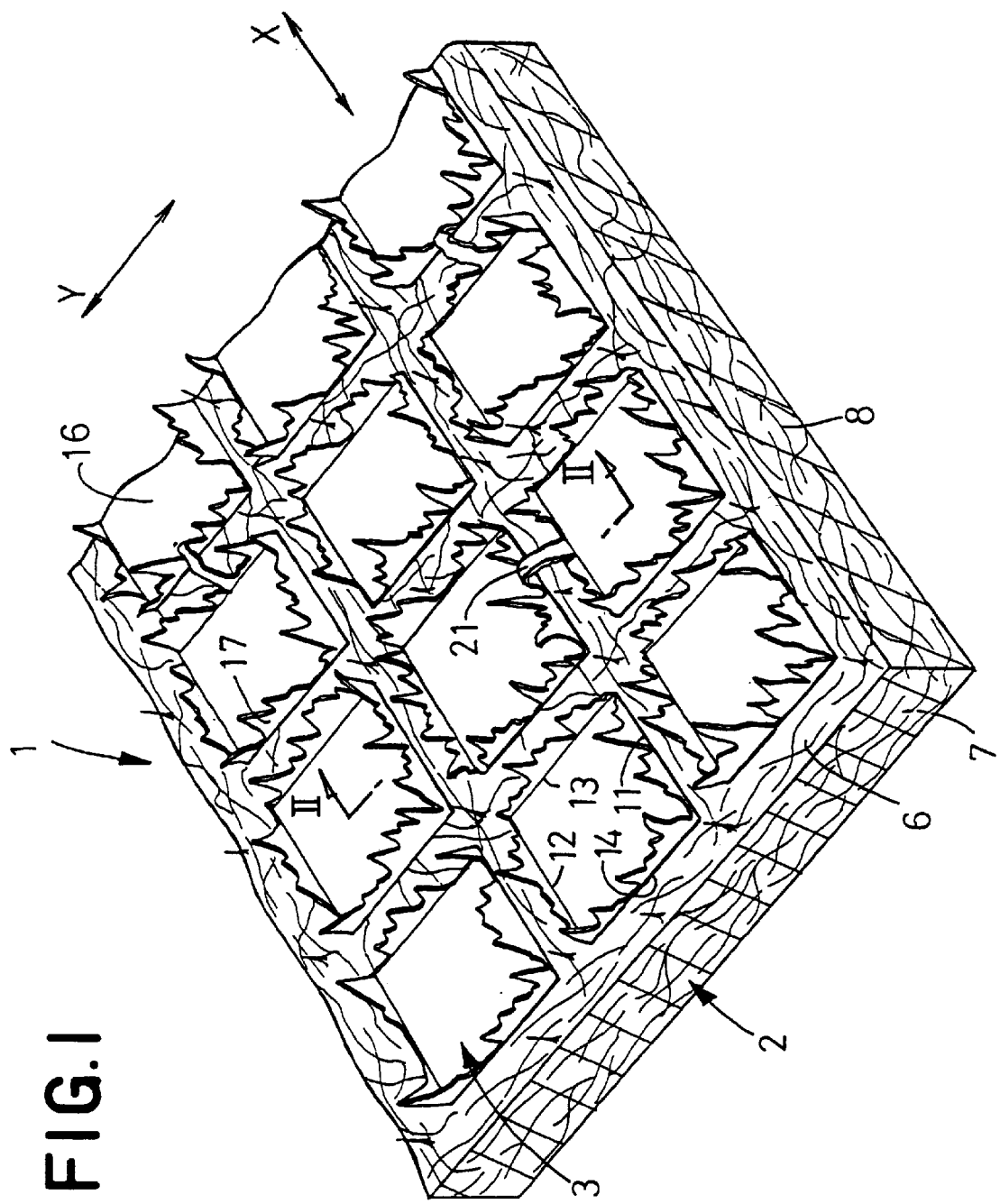
FIG. 1 is a perspective view of the composite sheet.
Figure 2:
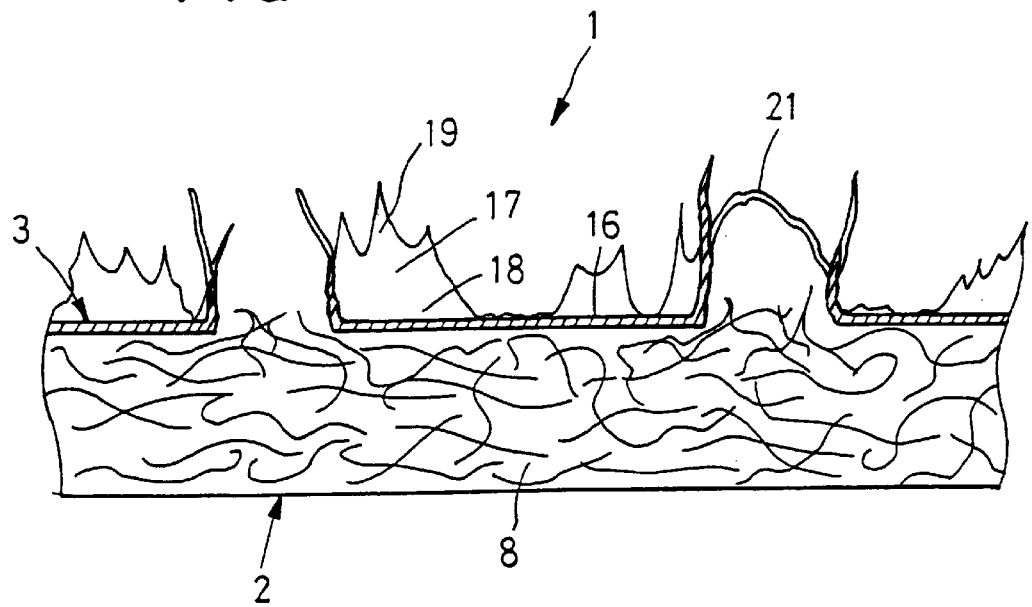
FIG. 2 is a sectional view taken along line II—II in FIG. 1.

FIG. 1 is a perspective view of the composite sheet 1 and FIG. 2 is a sectional view taken along line II—II in FIG. 1. The composite sheet 1 comprises a sheet-like fibrous assembly 2 having upper and lower surfaces 6, 7 and a plurality of narrow strips 3 of thermoplastic synthetic resin bonded to the upper surface 6.

The fibrous assembly 2 comprises fibers 8 such as thermoplastic synthetic fibers, chemical fibers or natural fibers and has a basis weight of 5~200 g/m². The fibers 8 are fused together or mechanically entangled together to maintain the assembly 2 in a sheet-like configuration. The fibers 8 preferably have a fineness of 0.5~20 dtex so far as these fibers 8 are of thermoplastic synthetic fibers. Examples of the fibrous assembly 2 include a spun bond nonwoven fabric, an air-through nonwoven fabric, a point bond nonwoven fabric, a melt blown nonwoven fabric and a spun lace nonwoven fabric. The fibrous assembly 2 preferably has a breathing-resistance lower than 0.2 kPa☐s/m.

The narrow strips 3 of the thermoplastic synthetic resin have a thickness of 1~50 µm and are arranged on the fibrous assembly 2 intermittently in a first direction X and in a second direction Y which is orthogonal to the first direction X. Each pair of the narrow strips being adjacent in the first direction X and in the second direction Y are spaced apart from each other by a distance of 30~1000 µm so that the upper surface 6 of the fibrous assembly 2 may be exposed between each pair of the adjacent narrow strips 3. When the composite sheet 1 is used as a topsheet in a disposable diaper, a sanitary napkin or the like, each of the narrow strips 3 is preferably shaped substantially in a quadrilateral, as in the embodiment depicted, defined by first and second sides 11, 12 extending parallel to each other in the first direction X and third and fourth sides 13, 14 extending parallel to each other in the second direction Y. Each of these sides 11~14 preferably has a length of 0.1~5 mm and each pair of the adjacent sides 11~14 preferably intersect each other at an angle of 20~160°.

Each side 11~14 of the narrow strip 3 are formed with a plurality of tooth-like portions 17 extending upward from its upper surface 16. The tooth-like portions 17 are made of the same material as the narrow strip 3 and have a thickness which is the same as or less than a thickness of the narrow strip itself. The tooth-like portions 17 have proximal ends 18 extending along the peripheral edge of the narrow strip 3 and distal ends 19 toward which the tooth-like portions 17 are tapered. These tooth-like portions 17 are arranged in the first direction X as well as in the second direction Y so as to surround the respective narrow strips 3. A height of the tooth-like portions 17 as measured from its proximal end 18 to its distal end 19 is preferably less than 1.5 mm.

These narrow strips 3 may be fused with or bonded to the fibrous assembly 2 and additionally, if desired, each pair of the adjacent narrow strips 3 may be connected by means of a bridge 21. Similarly to the tooth-like portions 17, the bridge 21 is made of the same material as the narrow strip 3 and has a proximal end extending along the peripheral edge of the narrow strip 3. The bridge 21 curves upward so as to described a circular arc.

The composite sheet 1 is useful as a liquid-pervious topsheet covering a liquid-absorbent core in a disposable diaper, a sanitary napkin. In this field of application, the composite sheet 1 preferably uses the hydrophilic fibers 8 and the hydrophilic or hydrophobic narrow strips 3. Body fluids discharged onto the upper surface of the composite sheet 1 are guided down between each pair of the adjacent narrow strips 3, 3 toward the bottom of the fibrous assembly 2 and absorbed by the absorbent core underlying the lower surface 7 of the assembly 2. The body fluids having been absorbed by the absorbent core are concealed by the narrow strips 3 and the tooth-like portions 17 and there is practically no anxiety that the absorbent core soiled with body fluids might be seen through when the diaper or the napkin is thrown away after it has been used. To improve this concealing effect of the composite sheet 1, the narrow strips 3 may be formed from thermoplastic synthetic resin containing suitable filler such as titanium oxide or barium sulfate by 1~30 wt %. The tooth-like portions 17 shake and diffusively reflecting the light incident thereupon and thereby serve to conceal the core stained with body fluids. A plurality of the tooth-like portions 17 are preferably formed along the respective sides 11~14.

The tooth-like portions 17 are flexibly deformed and thereby give a wearer's skin a velvet-like soft touch as the surface of the composite sheet 1 comes in contact with a wearer's skin. More specifically, the tooth-like portions 17 lying along the third and fourth sides 13, 14 are collapsed in the first direction X to give a wearer's skin the soft touch as a wearer's skin moves in the first direction X and rubs the composite sheet 1. Similarly, the tooth-like portions 17 lying along the first and second sides 11, 12 are collapsed in the second direction Y to give the wearer's skin said soft touch as the wearer's skin moves in the second direction Y and rubs the composite sheet 1. In this manner, the composite sheet 1 is flexible equally in both directions X, Y and the soft touch offered by the composite sheet 1 is not dependent on the direction. Thus, the composite sheet 1 can be used without caring about the anisotropy of flexibility.

When it is desired to use the composite sheet 1 as the liquid-pervious topsheet, a basis weight of the assembly 2 and a distance by which each pair of the adjacent narrow strips 3 are spaced apart from each other are preferably selected so that a breathing-resistance in the direction from the narrow strips 3 to the fibrous assembly 2 may be lower than 0.5 kPa·s/m.

Figure 3:
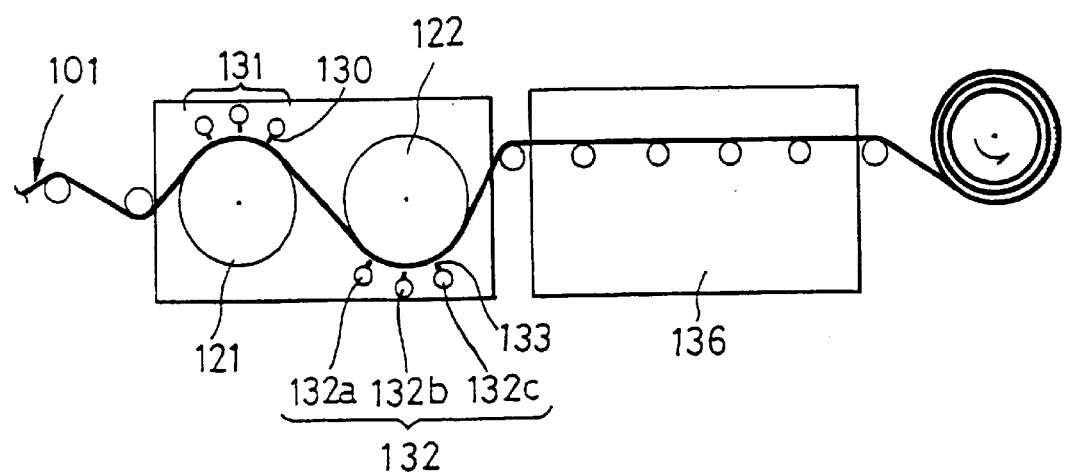
FIG. 3 is a fragmentary side view illustrating a process for making the composite sheet.
Figure 4:
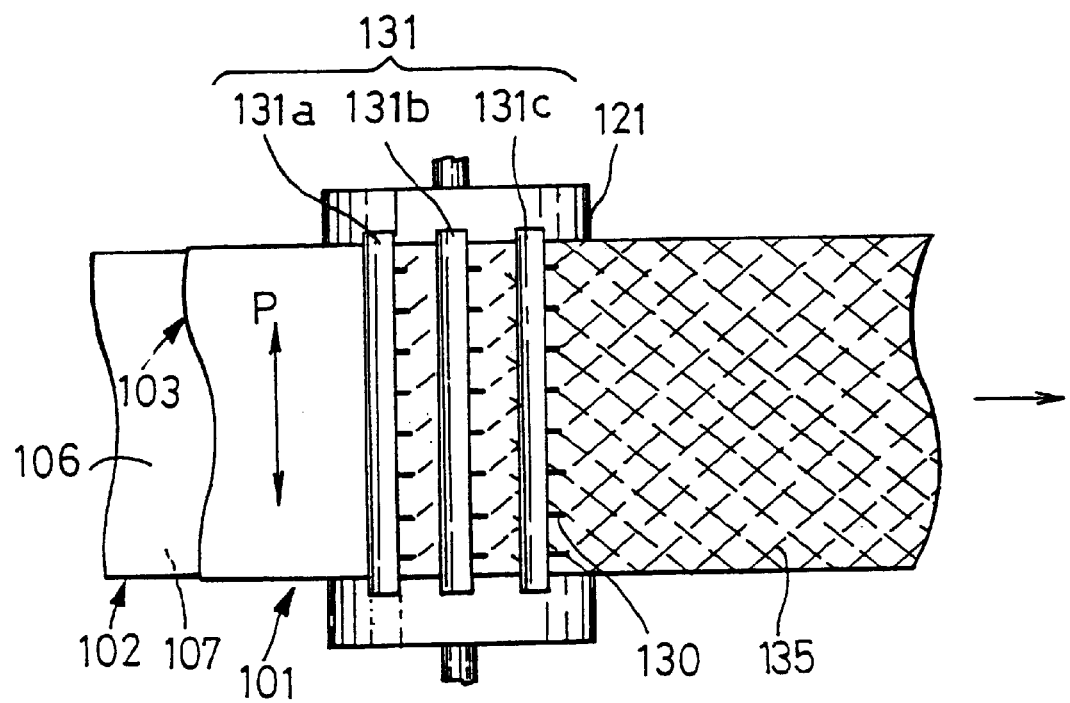
FIG. 4 is a fragmentary plan view depicting a part of FIG. 3.

FIG. 3 is a fragmentary side view illustrating a process for making the composite sheet and FIG. 4 is a fragmentary plan view depicting a part of FIG. 3. Referring to FIGS. 3 and 4, composite web 101 comprising fibrous web 102 and thermoplastic synthetic resin film 103 fused with or bonded to upper surface 106 of the fibrous web 102 is continuously fed from the left hand. The composite web 101 is brought from above into contact with a first rotary drum 121 provided around its peripheral surface with a plurality of water-pervious holes (not shown). Thereupon the composite web 101 is subjected to high pressure columnar water streams ejected from a plurality of nozzles 130 belonging to a first group of nozzles 131 arranged above the first rotary drum 121. The first group of nozzles 131 comprises a plurality of nozzle arrays 131$a$, 131$b$, 131$c$ extending transversely of the direction in which the composite web 101 is fed. These arrays respectively have a plurality of nozzles 130 adapted to repeat reciprocation over a desired dimension in a direction P orthogonal to the direction in which the composite web 101 is fed. Of the composite web 101 having been treated in this manner, the film 103 has been broken in accordance with movement loci of the respective nozzles 130 and consequently formed with a plurality openings 135. The composite web 101 formed with a plurality of openings 135 in this manner is then fed to a second rotary drum 122 provided around its peripheral surface with a plurality of liquid-pervious holes (not shown). The film 103 of the composite web 101 is brought from below into contact with the second rotary drum 122 and now a plurality of nozzles 133 belonging to a second group of nozzles 132 arranged below the second rotary drum 122 eject high pressure columnar water streams against lower surface 107 of the fibrous web 102. The second group of nozzles 132 also comprises a plurality of nozzle arrays 132$a$, 132$b$, 132$c$ extending transversely of the direction in which the composite web 101 is fed. These arrays respectively have a plurality of nozzles 133 adapted to repeat reciprocation over a desired dimension in a direction P orthogonal to the direction in which the composite web 101 is fed. The first and second groups of nozzles 131, 132 are substantially similar to each other with respect to the arrangement as well as to the manner in which these nozzles repeat reciprocation in the direction P. The high pressure columnar water streams ejected from the second group of nozzles 132 serve to widen and to lengthen the already formed openings 135 of the film 103. At the same time, the water streams serve to orient portions of the broken film remaining along the peripheral edges of the respective openings 135 so as to rise on the film 103. The portions having been oriented in this manner are depicted to form the tooth-like portions 17 and the bridges 21 depicted in FIGS. 1 and 2. Portions extending between each pair of the adjacent lengthened openings 135 are destined to form the narrow strips 3 depicted in FIGS. 1 and 2. The composite web 101 leaving the second rotary drum 122 toward the right passes through a dryer chamber 136 and is taken up into a roll of the composite sheet 1 depicted by FIG. 1.

The composite sheet 1 obtained in this manner offers a comfortable touch and reliably conceals the liquid-absorbent core stained with body fluids. From this viewpoint, the composite sheet according to this invention is suitable for use as the liquid-pervious topsheet of a disposable diaper or a sanitary napkin. This composite sheet is suitable also as the stock material for a disposable gown used in a medical field from a viewpoint of its comfortable touch and high breathability.

In the flexible composite sheet according to this invention, the narrow strips partially defining the surface of the sheet are formed along the entire peripheral edges thereof with a plurality of tooth-like portions. Such feature enables the surface of the composite sheet to offer a good flexibility independently of the direction in which a wearer's skin rubs the surface of the composite sheet.

What is claimed is:

1. A process for making a flexible composite sheet by subjecting a composite web comprising a continuous fibrous web having upper and lower surfaces and a continuous film of thermoplastic synthetic resin bonded to said upper surface to the steps of:

a. continuously feeding said composite web in one direction;

b. reciprocating a first group of nozzles in a direction transversely of said one direction, said first group of nozzles having a plurality of nozzles linearly arranged transversely of said one direction, wherein columnar fluid streams are ejected from said nozzles against said film of said composite web so that said film is broken in accordance with loci of said nozzles being reciprocated; and c. reciprocating a second group of nozzles in a direction transversely of said one direction, said second group of nozzles having a plurality of nozzles linearly arranged transversely of said one direction, wherein columnar fluid streams are ejected from said nozzles against said lower surface of said fibrous web so that broken regions of said film are widened and lengthened and portions of said film remaining along said broken regions are oriented so as to rise in a direction from said lower surface toward said upper surface of said fibrous web and form a plurality of discrete quadrilaterally-shaped portions of said thermoplastic synthetic resin film that are spaced apart from one another and arranged in an array on the upper surface of the fibrous layer.

2. The process according to claim 1, wherein said first and second groups of nozzles respectively comprises a plurality of nozzle arrays excluding parallel one to another.

3. The process according to claim 1, wherein said fluid streams comprise water streams.

* * * * *